United States Patent
Whitton

(10) Patent No.: US 10,660,925 B2
(45) Date of Patent: May 26, 2020

(54) METHOD FOR PRODUCING A MEDIUM CONTAINING STEROIDAL GLYCOSIDES FROM PLANT CELLS OF THE GENUS HOODIA

(71) Applicant: Lykke Research Limited, Darlington, Durham (GB)

(72) Inventor: Peter Andrew Whitton, Syston (GB)

(73) Assignee: LYKKE RESEARCH LIMITED, Darlington (GB)

( * ) Notice: Subject to any disclaimer, the term of this patent is extended or adjusted under 35 U.S.C. 154(b) by 133 days.

(21) Appl. No.: 15/773,295

(22) PCT Filed: Nov. 14, 2016

(86) PCT No.: PCT/GB2016/053560
§ 371 (c)(1),
(2) Date: May 3, 2018

(87) PCT Pub. No.: WO2017/081489
PCT Pub. Date: May 18, 2017

(65) Prior Publication Data
US 2018/0318368 A1   Nov. 8, 2018

(30) Foreign Application Priority Data

Nov. 13, 2015 (GB) .................................. 1520050.4

(51) Int. Cl.
| | | |
|---|---|---|
| A61K 36/24 | (2006.01) | |
| A61K 36/27 | (2006.01) | |
| A23L 2/60 | (2006.01) | |
| A23L 27/30 | (2016.01) | |
| A23L 33/105 | (2016.01) | |
| A23L 2/52 | (2006.01) | |
| A61K 31/704 | (2006.01) | |
| C12N 5/04 | (2006.01) | |

(52) U.S. Cl.
CPC .............. *A61K 36/24* (2013.01); *A23L 2/52* (2013.01); *A23L 2/60* (2013.01); *A23L 27/36* (2016.08); *A23L 33/105* (2016.08); *A61K 31/704* (2013.01); *A61K 36/27* (2013.01); *C12N 5/04* (2013.01); *A23V 2002/00* (2013.01); *A61K 2236/00* (2013.01); *A61K 2236/331* (2013.01); *A61K 2236/53* (2013.01)

(58) Field of Classification Search
None
See application file for complete search history.

(56) References Cited

U.S. PATENT DOCUMENTS

| 4,562,250 A | 12/1985 | Staba et al. |
| 6,376,657 B1 | 4/2002 | Van Heerden et al. |
| 2008/0261310 A1 | 10/2008 | Okole |

FOREIGN PATENT DOCUMENTS

| EP | 2329836 A1 * | 6/2011 | ............... A01H 4/00 |
| EP | 2329836 A1 | 6/2011 | |
| WO | WO2005/116049 A1 | 12/2005 | |
| WO | WO2006051334 A1 | 5/2006 | |

OTHER PUBLICATIONS

European Patent Office, International Searching Authority, International Search Report, PCT/GB2016/053560, dated Feb. 3, 2017, pp. 1-9, European Patent Office, Netherlands.

Zhou, Haidong; Ni, Jinren; Huang, Wen; Zhang, Jiandong; Separation of Hyaluronic Acid From Fermentation Broth by Tangential Flow Microfiltration and Ultrafiltration; Separation and Purification Technology; 2006; pp. 29-38; vol. 52; Elsevier B.V.; Amersterdam, Netherlands.

Veeresham Ciddi, Venkatesh Srinivasan, M.L. Shuler, Elicitation of *Taxus* sp. Cell Cultures for Production of Taxol, Biotechnology Letters, Dec. 1995, p. 1343-1346, vol. 17, No. 12, Springer Netherlands, Netherlands.

Giulliano Delle Monache, Maria Cristina De Rosa, Rosalba Scurria, Alberto Vitali, Angela Barbara Cuteri, Barbara Monacelli, Gabriella Pasqua, Bruno Botta, Comparison Between Metabolite Productions in Cell Culture and in Whole Plant of Maclura Pomifera, Phytochemistry, 1995, p. 575-580, vol. 39, No. 3, Elsevier Science Ltd., Great Britain.

R. Verpoote, R. Van Der Heijden, J. Schripsema, J.H.C. Hoge, H.J.G. Ten Hoopen, Plant Cell Biotechnology for the Production of Alkaloids: Present Status and Prospects, Journal of Natural Products, Feb. 1993, p. 186-207, vol. 56, No. 2, American Chemical Society, United States.

* cited by examiner

*Primary Examiner* — Heidi Reese
(74) *Attorney, Agent, or Firm* — Thomas B. McGurk

(57) ABSTRACT

A method for producing an active ingredient-containing medium from cultured plant cells, selected from the *Hoodia* genus, is provided. The method comprises the steps of: (i) incubating a mixture of cultured plant cells of the genus *Hoodia* and a liquid media in light; (ii) separating the incubated mixture into a first portion and a second portion; (iii) passing the first portion through a tangential flow filter to produce a filtrate containing only media and a retentate containing cultured plant cells; (iv) passing the filtrate through a nano-filter to obtain a nano-retentate having a high concentration of steroidal glycosides; (v) reintroducing some of the nano-retentate into the second portion; and (vi) repeating steps (i) to (v) using the second portion. The medium may be either plant cells or a plant extract.

13 Claims, No Drawings

METHOD FOR PRODUCING A MEDIUM CONTAINING STEROIDAL GLYCOSIDES FROM PLANT CELLS OF THE GENUS *HOODIA*

This application is a national stage filing under 35 U.S.C. § 371 of International Application No. PCT/GB2016/053560 filed on Nov. 14, 2016. This application claims priority of United Kingdom Patent Application No. 1520050.4 filed on Nov. 13, 2015 and International Application No. PCT/GB2016/052112 filed on Jul. 13, 2016. Both of the above listed applications are incorporated by reference in their entirety herein.

FIELD OF THE INVENTION

The present invention relates to a method for the production of a medium having high levels of steroidal glycosides. The medium may consist of a plant extract or plant cells and may be useful for example as an appetite suppressant.

BACKGROUND OF THE INVENTION

It is well established that extracts obtainable from plants of the Asclepiadaceae family, particularly the *Hoodia* genus (formerly the *Hoodia* and *Trichocaulon* genera) have been shown to have an appetite suppressant activity associated with specific steroidal glycosides. U.S. Pat. No. 6,376,657 discloses that these plants contain steroidal glycosides according to Formula 1:

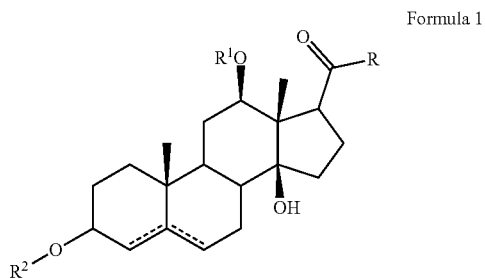

Formula 1 wherein:
R=alkyl;
$R^1$=H, alkyl, tigloyl, benzoyl or any other organic ester group;
$R^2$=H or one or more 6-deoxy carbohydrates, or one or more 2,6-dideoxy carbohydrates, or glucose radicals or combinations thereof;
and wherein the broken lines indicate the optional presence of a further bond between carbon atoms C4 and C5 or between carbon atoms C5 and C6.

U.S. Pat. No. 6,376,657 also discloses processes to extract steroidal glycosides according to Formula 1 from *Hoodia* plants, which involves treating plant material with a solvent to extract a fraction having appetite suppressant activity, separating the extraction solution from the rest of the plant material, removing the solvent from the extraction solution, optionally treating the solution with the additional solvent, and recovering the extract. The solvents specifically disclosed include methylene chloride, also known as dichloromethane. The patent also discloses methods for synthesizing various steroidal glycosides.

WO2005/116049 discloses that steroidal glycosides can be extracted or separated from undesirable components present in plant material of the Asclepiadaceae family by means of liquid or supercritical carbon dioxide extraction.

However, the use of a plant extract derived from an intact plant or parts of an intact plant has a number of disadvantages. Firstly, sufficient amounts of plant material have to be obtained for the extraction process. Harvesting is limited to a very few countries where the correct natural conditions are present to allow *Hoodia* to grow naturally. Outside of these countries, *Hoodia* can only be grown in specialised conditions in a greenhouse with great difficulty. Furthermore, *Hoodia* plants have a long life cycle and therefore, growing large quantities of plant material is not only expensive but also time consuming.

It is well known in the art that plant cells can be maintained and grown in tissue culture. Tissue culture is a term used in the art to define the growth of plant cells outside an intact plant in a suitable nutrient medium. Tissue culture is defined as a method wherein parts of a plant are transferred to an artificial environment in which they can continue to survive. The term tissue culture as understood in the art refers to cultured tissue which may consist of individual or groups of plant cells, protoplasts or whole or parts of a plant organ.

In tissue culture, plant cells can be grown on a solid surface as or as individual or small clusters of cells in suspension cultures. Cells grown in culture are actively dividing and can be maintained indefinitely in an undifferentiated state by transferring the cells to fresh media (sub-culturing). Cultured cells can also be induced to re-differentiate into whole plants. It has been shown that whole plants regenerated from callus cultures produce genetic variants.

Tissue culture is a method well known in the field of plant biology and has several applications, for example it is used to produce large quantities of plants or plant material by vegetative multiplication in a short period of time (micropropagation). Plant tissue cultures can be initiated from almost any part of the source plant (termed explant), although younger parts of a plant are generally more useful as they contain a higher amount of dividing cells. Although tissue culture is a method well known in the art, different plants may vary in the exact conditions for maintaining cells in culture. Cells in tissue culture are generally different from in vivo cells (cells in an intact plant which have not been isolated from the plant and cultured), for example they have a small vacuole, lack chloroplasts and photosynthetic pathways. It is also well known in the art that cultured plant cells produce different amounts and altered profiles of metabolites.

One way of tissue culturing plant cells is by suspension culture, which is disclosed in WO2006/051334. In a suspension culture, small clusters of cells are grown in a flask suspended in a culture media. The culture or nutrient media typically comprise carbohydrates as a source of energy, salts, vitamins, amino acids, minerals, plant growth hormones and other compounds. The flasks containing the cells and the culture media are typically stored on a shaker to prevent the cells from settling at the bottom of the flask. Suspension cultures are sub-cultured at specified intervals, for example every three weeks, to provide fresh growth media and to maintain the cells in an undifferentiated state. The cells obtained are treated by freeze drying, spray drying, vacuum drying or homogenisation techniques following culturing in order to change the physical nature of the cells. The cells can further be treated with one or more solvents in order to collect an extract fraction comprising at least one compound having appetite suppressant activity.

However, a significant problem with such techniques is that the use of solvents, such as alcohols, can denature the active ingredients (steroidal glycosides) within the plant extracts. The need remains therefore for alternate processes of obtaining therapeutically useful materials having a high content of steroidal glycosides which are suitable for use in foods, beverages or supplements.

EP2329836 A1 purports to disclose a process for the preparation of a plant extract from *Hoodia gordonii* suitable for use as an appetite suppressant. However, upon detailed examination of the document it is clear that the disclosure of EP23289836 is deficient and any extract produced according to the processes disclosed in EP2329836 will not actually contain therapeutically significant amount of steroidal glycosides.

It is well known that the steroidal glycosides in *Hoodia gordonii* are generated within the plant to protect it from UV damage. In the absence of a UV light source only a relatively small amount of steroidal glycosides is generated. For example, U.S. Pat. No. 4,562,250 discloses that much greater quantities of steroidal glycosides are generated in *Yucca* cell cultures that grown in light than are grown in darkness. EP2329836 discloses four alternative methods of preparing *Hoodia gordonii* plant extracts: examples 1 to 4 on page 6 of the specification. In each of these examples a cell line of *Hoodia gordonii* is grown in the dark at a temperature of 25° C. for 14 days. Crucially, all of the cell lines are grown in the dark without any light source. It is an inevitable outcome of being grown in the dark that the resulting cells will contain only relatively low levels of steroidal glycosides.

As the extracts of EP2329836 contain only low levels of steroidal glycosides it must be assumed that the demonstrated appetite suppressing and fungicidal effects of those extracts cannot be due to therapeutic levels of steroidal glycosides in the extracts. Rather, any such effects must be due to the presence of other chemicals or components in the extracts, for example solvents that are used to extract the steroidal glycosides.

Tangential flow (or crossflow) filtration technique (TFF) is an effective method to separate or remove cell debris, and recover biosynthetic substances after bacterial fermentation ('Separation of hyaluronic acid from fermentation broth by tangential flow microfiltration and ultrafiltration', Zhou et al, Separation and Purification Technology (2006), No 52, pp. 29-38). In TFF, bulk flows tangentially across a membrane and perpendicularly to a permeation flux. The filtering performance of TFF depends on the properties of the membrane, the product and operational conditions such as trans-membrane pressure, crossflow velocity, solution chemistry, concentration factor and running time etc. TFF is usually considered to be effective on the condition that solutes differ by more than a 10-fold difference in size. High performance TFF (HPTFF) has also been developed to achieve separation of solutes differing by less than a 10-fold difference in size according to Zhou et al.

In light of all of the above there is need for an improved method of obtaining a medium containing steroidal glycosides that is suitable for therapeutic use as an appetite suppressant or for any other appropriate use.

SUMMARY OF THE INVENTION

The present invention provides a method for producing a medium containing steroidal glycosides from plant cells of the genus *Hoodia*, the method comprising the steps of:

(i) incubating a mixture of cultured plant cells of the genus *Hoodia* and a liquid media in light;
(ii) separating the incubated mixture into a first portion and a second portion;
(iii) passing the first portion through a tangential flow filter to produce a filtrate containing only media and a retentate containing cultured plant cells;
(iv) passing the filtrate through a nano-filter to obtain a nano-retentate having a high concentration of steroidal glycosides;
(v) reintroducing some of the nano-retentate into the second portion; and
(vi) repeating steps (i) to (v) using the second portion.

The method of the present invention is advantageous in that it provides an optimised and repeatable method of producing a medium containing usable levels of steroidal glycosides. In particular, the method is advantageous as it can ensure that the plant cells are cultured in a media containing high levels of steroidal glycosides, thereby maximising the amount of steroidal glycosides in both the media and the plant cells. This is achieved by maintaining a high level of steroidal glycosides in the media by reintroducing some of the nano-retentate into the second portion and repeating steps (i) to (v) using the second portion.

When steps (i) to (v) are repeated this may be done by using only the second portion with added nano-retentate i.e. the product of step (v). Alternatively, additional cultured plant cells and/or liquid media may be added to the product of step (v) before steps (i) to (v) are repeated. In this manner the method of the present invention may be carried out for substantially any number of iterations.

That medium may consist of cultured plant cells of the genus *Hoodia* having maximised levels of steroidal glycosides i.e. the retentate of step (iii). Alternatively, the medium may consist of a plant extract i.e. the nano-retentate of step (iv).

The method of the present invention is advantageous in that it can produce cultured plant cells that have saturation or near saturation levels of steroidal glycosides. In particular, these cells are the retentate of step (iii). These plant cells can be used as a therapeutic product as on ingestion they will be broken down and will release the steroidal glycoside.

The method is also advantageous as it provides a method whereby the liquid media in which the cultured plant cells are incubated can be maintained with a high concentration of steroidal glycosides. This is achieved by reintroducing the some of the nano-retentate into the second portion. The second portion can then be re-used as the mixture of step (i). In this manner the liquid media of the mixture of step (i) will have a high level of steroidal glycosides, which will act to ensure that the level of steroidal glycosides within the cultured plant cells is high and may be at a saturation or near saturation level.

In methods according to the prior art, the steroidal glycosides of the nano-retentate would be the product of the method and the retentate of the tangential flow filter would be disposed of. The nano-retentate would be used directly as the product of the method and would not be reintroduced into the media.

If the medium of the present invention is the cultured plant cells that form the retentate of step (iii) it may be preferable that the method further comprises the step of freeze-drying said retentate to transform the plant cells into a more usable form. Further, if the plant cells are freeze-dried then it may be preferable to wash the freeze-dried cells to remove any media. For example, the freeze-dried cells may be washed in distilled water. This may be preferable as the media may contain chemicals that are ideally not ingested such as polar solvents e.g. ethanol.

In order to ensure that the sufficient steroidal glycosides are produced by the cultured plant cells during step (i) it is preferable that the plant cells are incubated for a duration of at least 5 days. Incubation may be carried out for longer periods if desired.

In order for the retentate of step (iii) to contain substantially all of the cultured plant cells of the first portion the pore size of the tangential flow filter should be such that the cultured plant cells cannot pass therethrough. In particular, the pore sizes should be smaller than the cell nuclei of the cultured plant cells, the rest of the cell being flexible and able to squeeze through pores. The cell nuclei of the cultured plant cells are approximately 5 microns to 10 microns in diameter. Therefore, it may be preferable that the pore size of the tangential flow filter are 3.5 microns or less, for example between 0.01 and 3.5 microns. More preferably the tangential flow filter may have a 0.2 micron pore size.

The purpose of the nano-filter of step (iv) is to retain substantially all of the steroidal glycosides in the nano-filtrate. In order to achieve this the nano-filter is preferably formed to have a molecular weight cut off (MWCO) that is less than the size of the steroidal glycosides. This can be achieved by having a nano-filtration membrane with a suitable MWCO. For example, the MWCO off the nano-filter may be 5,000 kDa.

The species of the *Hoodia* genus can be any suitable species that produces significant amounts of steroidal glycosides. For example, the genus may be selected from *Hoodia gordonii*, *Hoodia currorii* or *Hoodia lugardi*.

The medium produced by the method of the present invention can be used in any manner apparent to the person skilled in the art. For example, they may be used as an appetite suppressant for the treatment of obesity or any other condition where appetite suppression is desirable. The plant cells may be used to form part of a foodstuff, beverage, or dietary supplement for appetite suppression.

It has also been shown that the compounds in *Hoodia* extracts of plant material can be used in the manufacture of a medicament for the treatment and/or prevention of diabetes. Accordingly, a skilled person will also understand that a medium produced by the method of the present invention can be used in the manufacture of a medicament for the treatment and/or prevention of diabetes.

The use of cultured plant cells produced by the method of the present invention as a medicament may provide an advantage over the use of a plant extract obtained by methods described in the art. The cultured plant cells may simply be harvested and used for, for example, oral administration or as food supplements. In a preferred embodiment of the invention, cultured plant cells may be used in the manufacture of the medicament.

The medium of the present invention be used to formulate as liquid dosage forms which include solutions, suspensions and emulsions.

If the medium produced by the method of the present invention is used for therapeutic use they are to be administered to human subjects in "therapeutically effective amounts", which is taken to mean a dosage sufficient to provide a medically desirable result in the patient. The exact dosage and frequency of administration of a "therapeutically effective amount" of active agent will vary, depending on the condition which it is desired to treat, the stage and severity of disease, and such factors as the nature of the active substance, the dosage form and route of administration. According to the present invention, cultured plant cells of the genus *Hoodia* and/or pharmaceutical compositions containing these plant cells may be used as an appetite suppressant for the prevention (e.g. prophylaxis) and/or treatment of a disease associated with weight gain (which for the purposes herein in its broadest sense also includes preventing, treating and/or alleviating the symptoms and/or complications of such disease).

Generally a medium prepared according to the method invention and used as an appetite suppressant, or a pharmaceutical composition, foodstuff, beverage or supplement comprising the plant cells, will not contain ethanol or a non-polar solvent. A person skilled in the art will appreciate that a non-polar solvent is one with a dielectric constant of less than 15, such as pentane, cyclopentane, hexane, cyclohexane, benzene, toluene, 1,4-dioxane, chloroform, diethyl ether or dichloromethane (DCM).

The invention will be further understood with reference to the following non-limiting experimental example. Methods of obtaining a medium according to steps 1-3 are well known in the art and do not form part of the invention.

EXAMPLE

Step 1: Initiation of Callus Cultures from *Hoodia*: Preparation of Callus Induction Media
Callus Induction Media Solution
Distilled $H_2O$ to 100%
3.0% sucrose
1.0% NAA (naphthalene acetic acid) 0.004% stock solution
0.44% Murashige and Skoog Basal powdered medium
Equipment
Glass bottle with cap
Magnetic stirrer
Sterile plastic plant culture dishes
Glass pipettes
pH meter
Autoclave
Laminar flow cabinet
Balance
Nescofilm
Phytagel
1M NaOH solution
0.1M NaOH solution
Method
Callus induction media was prepared using Murashige and Skoog (MS) media obtained from Sigma, with 3% sucrose and 1% naphthalene acetic acid (from a concentrated stock solution of 0.004% w/v). The pH of the prepared media was adjusted to pH 5.75 and solidified with 0.2% phytagel. The media was autoclaved for 20 mins at 121° C. and then poured out into sterile plastic plant tissue culture dishes.

Step 2: Initiation of callus cultures from *Hoodia*: sterilisation of plant tissue
Reagents
Media prepared previously (according to Example 1)
*Hoodia gordonii* plant tissue
Equipment
Sterile glass beakers
Sterile distilled water
Sterile scalpel
Sterile tweezers
10% bleach solution
70% ethanol solution
1M NaOH solution
0.1M NaOH solution Method Plant tissue of *Hoodia* was sterilised by immersion in 70% ethanol for 2 minutes, followed by immersion in 10% bleach solution for 10 minutes. *Hoodia* was then washed three times with sterile (autoclaved) distilled water. The sterile *Hoodia* was aseptically cut into disk shapes in a sterile laminar flow cabinet. *Hoodia* slices were placed onto the prepared plates containing callus induction media, and the plates were sealed with Nescofilm. The plates were placed in the dark at 27° C. and callus formation began to appear after about 1 month.

Step 3: Media Preparation for Established Cultures

Reagents

Distilled $H_2O$ to 100%

3% sucrose 0.44% Murashige and Skoog Basal powdered medium

1% NAA (naphthalene acetic acid) 0.004% stock solution 0.01% Vitamin solution (0.05% pyridoxal hydrochloride, 0.10% thiamine dichloride and 0.05% nicotinic acid)

1M NaOH solution 0.1M NaOH solution

Equipment

1 L glass bottle

Magnetic stirrer

20×250 m conical flasks

20× sheets of foil approximately 20×20 cm

Glass pipettes pH meter

Autoclave

Laminar flow cabinet

Balance

Method

Mix 3% sucrose, 0.44% MS powder, 1% NAA stock and 0.01% vitamin stock and prepare to 100% with distilled $H_2O$. Mix using a magnetic stirrer until all dry components dissolved, then adjust the pH with 1M and 0.1M NaOH, to pH 5.75. Take 20 250 ml conical flasks. To each add 50 ml media and the seal neck of flask with foil. Sterilize in autoclave, at 121° C., 103 kPa, for 25 minutes. Immediately following sterilization, place the flasks in laminar flow cabinet and allow to cool to ambient temperature.

Step 4: Inoculation, Subculture and Production of Active Ingredient of Established Cultures Reagents Friable callus 70% Ethanol Equipment Laminar flow cabinet Bunsen burner Prepared media 20× sterile sheets of foil approximately 20×20 cm Several pairs of tweezers or small forceps Wide spatulas with holes Peristaltic pump Sartorius Viva flow 200 system 5000 MWCO (Fisher Scientific, Loughborough)

Method

Sterilize inside of laminar flow cabinet with 70% ethanol. Sterilize all tweezers and spatulas by dipping in 70% ethanol, then flaming till red hot. Allow to cool inside laminar flow cabinet.

Initial Inoculation:

Remove foil from prepared media flask. Take sterilized tweezers and remove thumbnail sized pieces of friable callus from the plant tissue. Break up into finely dispersed cells and add to flask. Aim to add approximately 5 g tissue to 50 ml media (10% w/v). Flame the neck of the flask, and cover with a sterile sheet of foil. Place the flask on a shaker at 120 rpm, in a dark room heated to 27° C. Leave until a thick, dispersed cell suspension culture can be observed (approximately 2 weeks).

Subculture:

Remove foil from prepared media flask. Remove foil from flask containing dispersed cell suspension cultures (produced by initial inoculation). Take wide spatula with holes, sterilize, allow to cool and scoop out the cells. Add these cells to the fresh media. Aim to add approximately 5 g tissue to 50 ml media. Flame the neck of the flask, and cover with a sterile sheet of foil. Place the flask on a shaker at 120 rpm, in a dark room heated to 27° C. After 14 days, use the cell suspension culture for further subcultures.

Production of Medium

Take the flasks after the 14 days incubation and place in daylight. Incubate in daylight for 5 days. Split the content of the flasks into a first portion and a second portion of substantially equal volumes. Retain the second portion in a separate flask for further use. Pass the first portion through a tangential filter with 0.2 micron pore size to obtain a filtrate and a retentate. The retentate will substantially consist of cultured plant cells with a high steroidal glycoside content. The retentate is freeze-dried then rinsed of any remaining media with water to avoid undesirable compounds in the media. The resulting free-dried cultured plant cells are then used as an appetite suppressant.

Pass the filtrate through a viva flow membrane with MWCO 5,000 kDa under reduced flow rate and pressure (10% of the recommended flow rate). Collect the retentate from this filter and reintroduce into the second portion. Discard the filtrate. A portion of the retentate may be retained and used as a plant extract containing steroidal glycosides.

Repetition of Previous Step

Repeat method as set out immediately above using the second portion. If necessary add further liquid media and/or subculture as produced in the preceding step.

The invention claimed is:

1. A method for producing a composition containing steroidal glycosides from plant cells of the genus *Hoodia*, the method comprising the steps of:
   incubating a mixture comprising cultured plant cells of the genus *Hoodia* and a liquid media in light;
   (ii) separating the incubated mixture into a first portion and a second portion;
   (iii) passing the first portion through a tangential flow filter to produce a filtrate comprising liquid media and a retentate comprising cultured plant cells;
   (iv) passing the filtrate through a nano-filter to obtain a nano-retentate comprising a saturation level of steroidal glycosides;
   (v) reintroducing a portion of the nano-retentate into the second portion; and
   (vi) repeating steps (i) to (v) using the second portion.

2. The method of claim 1, wherein the composition comprises cultured plant cells of the retentate of step (iii).

3. The method according to claim 2, further comprising the step:
   (iii-a) freeze-drying the retentate.

4. The method according to claim 3, further comprising the step:
   (iii-b) washing the freeze-dried retentate in water to remove remaining liquid media.

5. The method of claim 1, wherein the composition is a plant extract comprising the nano-retentate of step (iv).

6. The method according to claim 1, wherein the incubating step lasts for a duration of at least 5 days.

7. The method according to claim 1, wherein the tangential flow filter has a pore size membrane between 0.01 microns and 3.5 microns.

8. The method of claim 7, wherein the tangential flow filter has a pore size membrane between 0.1 and 0.3 microns.

9. The method of claim 7 wherein the tangential flow filter has a 0.2 micron pore size membrane.

10. The method according to claim 1, wherein a nano-filtration membrane of the nano-filter has a molecular weight cut off of 5,000 kDa.

11. The method according to claim 1, wherein the species of the *Hoodia* genus is selected from *Hoodia gordonii*, *Hoodia currorii* or *Hoodia lugardi*.

12. A composition produced by the method according to claim 1 for use as an appetite suppressant.

13. A foodstuff, beverage or supplement comprising the composition of claim 2.

* * * * *